(12) United States Patent
Endell et al.

(10) Patent No.: US 9,579,378 B2
(45) Date of Patent: Feb. 28, 2017

(54) COMBINATIONS AND USES THEREOF

(71) Applicant: MORPHOSYS AG, Martinsried/Planegg (DE)

(72) Inventors: Jan Endell, Munich (DE); Lisa Rojkjaer, Hedingen (CH)

(73) Assignee: MORPHOSYS AG, Planegg-Martinsried (DE)

( * ) Notice: Subject to any disclaimer, the term of this patent is extended or adjusted under 35 U.S.C. 154(b) by 0 days.

(21) Appl. No.: 14/430,801

(22) PCT Filed: Sep. 24, 2013

(86) PCT No.: PCT/EP2013/069858
§ 371 (c)(1),
(2) Date: Mar. 24, 2015

(87) PCT Pub. No.: WO2014/048921
PCT Pub. Date: Apr. 3, 2014

(65) Prior Publication Data
US 2015/0238603 A1      Aug. 27, 2015

Related U.S. Application Data

(60) Provisional application No. 61/705,172, filed on Sep. 25, 2012, provisional application No. 61/774,595, filed on Mar. 8, 2013.

(51) Int. Cl.
| A61K 38/00 | (2006.01) |
| A61K 39/395 | (2006.01) |
| C07K 16/28 | (2006.01) |
| A61K 31/198 | (2006.01) |
| A61K 39/00 | (2006.01) |

(52) U.S. Cl.
CPC ...... *A61K 39/39558* (2013.01); *A61K 31/198* (2013.01); *A61K 39/3955* (2013.01); *C07K 16/2896* (2013.01); *A61K 2039/545* (2013.01)

(58) Field of Classification Search
None
See application file for complete search history.

(56) References Cited

U.S. PATENT DOCUMENTS

2002/0164788 A1    11/2002    Ellis

FOREIGN PATENT DOCUMENTS

| WO | 9962526 | 12/1999 |
| WO | 0040265 | 7/2000 |
| WO | 0206347 | 1/2002 |
| WO | 2005103083 | 11/2005 |
| WO | 2006099875 | 9/2006 |
| WO | 2006125640 | 11/2006 |
| WO | 2007042309 | 4/2007 |
| WO | 2008037257 | 4/2008 |
| WO | 2008047242 | 4/2008 |
| WO | 2010061357 | 6/2010 |
| WO | 2010061358 | 6/2010 |
| WO | 2010061359 | 6/2010 |
| WO | 2010061360 | 6/2010 |
| WO | 2011/154453 | * 12/2011 |
| WO | 2012041800 | 4/2012 |
| WO | WO 2012/076663 | 6/2012 |
| WO | WO 2012/092616 | 7/2012 |
| WO | WO 2013/002879 | 1/2013 |
| WO | WO 2014/159911 | 10/2014 |
| WO | WO 2014/178820 | 11/2014 |

OTHER PUBLICATIONS

George et al. (Circulation. 1998; 97: 900-906).*
Lippincott-Schwartz (Current Protocols in Cell Biology, 16.0.1-16.0.2, 2002).*
Clarke, Breast Cancer Research and Treatment vol. 46 p. 255 (1997).*
PCT/EP2013/069858 ISR dated on Nov. 18, 2013.
PCT/EP2013/069858 WOSA dated on Nov. 18, 2013.
PCT/EP2013/069858 IPRP dated on Mar. 31, 2015.

* cited by examiner

*Primary Examiner* — Sheela J Huff
(74) *Attorney, Agent, or Firm* — Seyfarth Shaw LLP (57) ABSTRACT

The present disclosure describes a pharmaceutical combination of an anti-CD38 antibody and melphalan.

16 Claims, 4 Drawing Sheets

The amino acid sequence of the MOR202 Variable Heavy Domain is:

QVQLVESGGGLVQPGGSLRLSCAASGFTFSSYYMNWVRQAPGKGLEWVSGIS GDPSNTYYADSVKGRFTISRDNSKNTLYLQMNSLRAEDTAVYYCARDLPLVYTGFA YWGQGTLVTVSS (SEQ ID NO: 7)

The DNA sequence encoding the MOR202 Variable Heavy Domain is:

CAGGTGCAATTGGTGGAAAGCGGCGGCGGCCTGGTGCAACCGGGCGGCAG
CCTGCGTCTGAGCTGCGCGGCCTCCGGATTTACCTTTTCTTCTTATTATATGAATTG
GGTGCGCCAAGCCCCTGGGAAGGGTCTCGAGTGGGTGAGCGGTATCTCTGGTGAT
CCTAGCAATACCTATTATGCGGATAGCGTGAAAGGCCGTTTTACCATTTCACGTGA
TAATTCGAAAAACACCCTGTATCTGCAAATGAACAGCCTGCGTGCGGAAGATACG
GCCGTGTATTATTGCGCGCGTGATCTTCCTCTTGTTTATACTGGTTTTGCTTATTGG
GGCCAAGGCACCCTGGTGACGGTTAGCTCA (SEQ ID NO: 8)

The amino acid sequence of the MOR202 Variable Light Domain is:

DIELTQPPSVSVAPGQTARISCSGDNLRHYYVYWYQQKPGQAPVLVIYGDSKR PSGIPERFSGSNSGNTATLTISGTQAEDEADYYCQTYTGGASLVFGGGTKLTVLGQ (SEQ ID NO: 9)

The DNA sequence encoding the MOR202 Variable Light Domain is:

GATATCGAACTGACCCAGCCGCCTTCAGTGAGCGTTGCACCAGGTCAGACC
GCGCGTATCTCGTGTAGCGGCGATAATCTTCGTCATTATTATGTTTATTGGTACCAG
CAGAAACCCGGGCAGGCGCCAGTTCTTGTGATTTATGGTGATTCTAAGCGTCCCTC
AGGCATCCCGGAACGCTTTAGCGGATCCAACAGCGGCAACACCGCGACCCTGACC
ATTAGCGGCACTCAGGCGGAAGACGAAGCGGATTATTATTGCCAGACTTATACTG
GTGGTGCTTCTCTTGTGTTTGGCGGCGGCACGAAGTTAACCGTTCTTGGCCAG (SEQ ID NO: 10)

The amino acid sequence of the MOR202 HCDR1 is: GFTFSSYYMN (SEQ ID NO: 1)

The amino acid sequence of the MOR202 HCDR2 is: GISGDPSNTYYADSVKG (SEQ ID NO: 2)

The amino acid sequence of the MOR202 HCDR3 is: DLPLVYTGFAY (SEQ ID NO: 3)

The amino acid sequence of the MOR202 LCDR1 is: SGDNLRHYYVY (SEQ ID NO: 4)

The amino acid sequence of the MOR202 LCDR2 is: GDSKRPS (SEQ ID NO: 5)

The amino acid sequence of the MOR202 LCDR3 is: QTYTGGAS (SEQ ID NO: 6)

COMBINATIONS AND USES THEREOF

This application is a national stage entry of International Patent Application No. PCT/EP2013/069858, filed Sep. 24, 2013, which claims priority to U.S. provisional patent application No. 61/705,172, filed Sep. 25, 2012 and to U.S. provisional patent application No. 61/774,595, filed Mar. 8, 2013, the disclosures of each of which are herein incorporated by reference in their entireties.

FIELD

The present disclosure describes a pharmaceutical combination of an anti-CD38 antibody and melphalan.

BACKGROUND

Multiple myeloma is a B cell malignancy characterized by the latent accumulation in bone marrow of secretory plasma cells with a low proliferative index and an extended life span. The disease ultimately attacks bones and bone marrow, resulting in multiple tumors and lesions throughout the skeletal system.

Approximately 1% of all cancers, and slightly more than 10% of all hematologic malignancies, can be attributed to multiple myeloma (MM). Incidence of MM increases in the aging population, with the median age at time of diagnosis being about 61 years. Currently available therapies for multiple myeloma include chemotherapy, such as vincristine, BCNU, melphalan, cyclophosphamide, adriamycin, and prednisone or dexamethasone, stem cell transplantation, Thalomid® (thalidomide), Velcade® (bortezomib), Aredia® (pamidronate), and Zometa® (zoledronic acid). Current treatment protocols, which include a combination of chemotherapeutic agents, yield a complete remission rate of only about 5%, and median survival is approximately 36-48 months from the time of diagnosis. Recent advances using high dose chemotherapy followed by autologous bone marrow or peripheral blood mononuclear cell transplantation have increased the complete remission rate and remission duration. Yet overall survival has only been slightly prolonged, and no evidence for a cure has been obtained. Ultimately, MM patients often relapse, even under maintenance therapy with interferon-alpha (IFN-α) alone or in combination with steroids.

CD38 is an example of an antigen expressed on such malignant plasma cells. Functions ascribed to CD38 include both receptor mediation in adhesion and signaling events and (ecto-) enzymatic activity. As an ectoenzyme, CD38 uses NAD+ as substrate for the formation of cyclic ADP-ribose (cADPR) and ADPR, but also of nicotinamide and nicotinic acid-adenine dinucleotide phosphate (NAADP). cADPR and NAADP have been shown to act as second messengers for Ca2+ mobilization. By converting NAD+ to cADPR, CD38 regulates the extracellular NAD+ concentration and hence cell survival by modulation of NAD-induced cell death (NCID). In addition to signaling via Ca2+, CD38 signaling occurs via cross-talk with antigen-receptor complexes on T and B cells or other types of receptor complexes, e.g. MHC molecules, and is in this way involved in several cellular responses, but also in switching and secretion of IgG.

Today various approaches to target CD38 are disclosed in the art. For example antibodies specific for CD38 are described in WO1999/62526 (Mayo Foundation); WO200206347 (Crucell Holland); US2002164788 (Jonathan Ellis) which is incorporated by reference in its entirety; WO2005/103083, U.S. Ser. No. 10/588,568, which is incorporated by reference in its entirety, WO2006/125640, U.S. Ser. No. 11/920,830, which is incorporated by reference in its entirety, and WO2007/042309, U.S. Ser. No. 12/089,806, which is incorporated by reference in its entirety (MorphoSys AG); WO2006099875, U.S. Ser. No. 11/886,932, which is incorporated by reference in its entirety (Genmab); and WO08/047242, U.S. Ser. No. 12/441,466, which is incorporated by reference in its entirety (Sanofi-Aventis). However, in order to improve efficacy of CD38 antibodies, different combination therapies of antibodies specific for CD38 and other agents are already disclosed e.g. in WO200040265, U.S. Ser. No. 09/226,895, which is incorporated by reference in its entirety, (Research Development Foundation); WO2006099875 and WO2008037257, U.S. Ser. Nos. 11/886,932 and 12/442,808, which is incorporated by reference in its entirety, (Genmab); WO2012/041800 (MorphoSys AG) and WO2010061360, U.S. Ser. No. 13/131,389, which is incorporated by reference in its entirety, WO2010061359, U.S. Ser. No. 13/130,867, which is incorporated by reference in its entirety, WO2010061358, U.S. Ser. No. 13/130,865, which is incorporated by reference in its entirety, and WO2010061357, U.S. Ser. No. 13/130,862, which is incorporated by reference in its entirety, (Sanofi Aventis), which are all incorporated by reference in their entireties.

However many forms of cancer involving CD38-expressing tumors still have a poor prognosis and present therapies are not sufficient. Thus, there is a need for improved methods for treating such forms of cancer.

SUMMARY

Surprisingly, it was found that the combination of a particular anti-CD38 antibody with melphalan showed a synergistic level of reduced bone lysis in a clinically relevant multiple myeloma in vivo model. Due to its surprising synergistic effects, this combination provides an improved and promising approach for the treatment of multiple myeloma in humans.

In one aspect, the present disclosure relates to a synergistic combination of an antibody specific for CD38 and melphalan. In another aspect the present disclosure relates to a pharmaceutical composition comprising an antibody specific for CD38 and a nitrogen mustard alkylating agent. Such combinations are useful in the treatment of cancers involving tumor cells, such as, multiple myeloma.

Melphalan is a nitrogen mustard alkylating agent, therefore, other nitrogen mustard alkylating agents, such as, cyclophosphamide, mechlorethamine, uramustine, chlorambucil, ifosfamide or bendamustine may also lead to synergistic effects when used in combination with an anti-CD38 antibody.

Another aspect comprises the use of the synergistic combinations of an anti-CD38 antibody and a nitrogen mustard alkylating agent in the treatment of chronic lymphocytic leukemia, chronic myelogenous leukemia, acute myelogenous leukemia, and/or acute lymphocytic leukemia An aspect of the present disclosure comprises a combination wherein the antibody specific for CD38 comprises an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6)

and melphalan. In preferred aspects, the combination is used for the treatment of multiple myeloma.

DESCRIPTION OF DRAWINGS

FIG. 4 shows the amino acid sequence of MOR202.

DETAILED DESCRIPTION

Definitions

A "pharmaceutical composition" includes at least an active agent, e.g. an antibody for therapeutic use in humans. A pharmaceutical composition also includes a combination of active agents, e.g. an antibody for therapeutic use in humans and nitrogen mustard. A pharmaceutical composition may include acceptable carriers or excipients.

"Administered" or "administration" includes but is not limited to delivery by an injectable form, such as, for example, an intravenous, intramuscular, intradermal or subcutaneous route or mucosal route, for example, as a nasal spray or aerosol for inhalation or as an ingestible solution, capsule or tablet.

"Synergy", "synergism" or "synergistic activity" mean more than the expected additive effect of a combination. The "synergy", "synergism" or "synergistic activity" of a combination is determined herein by the method of Clarke et al. See Clarke et al., Issues in experimental design and endpoint analysis in the study of experimental cytotoxic agents in vivo in breast cancer and other models, Breast Cancer Research and Treatment 46:255-278 (1997), which is incorporated by reference in its entirety.

The term "antibody" means monoclonal antibodies, including any isotype, such as, IgG, IgM, IgA, IgD and IgE. An IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are referred to as CDR1, CDR2, and CDR3, numbered sequentially from the N-terminus. The more highly conserved portions of the variable regions outside of the CDRs are called the "framework regions". An "antibody fragment" means an Fv, scFv, dsFv, Fab, Fab' F(ab')2 fragment, or other fragment, which contains at least one variable heavy or variable light chain, each containing CDRs and framework regions. An "antigen binding fragment" is an antibody fragment that binds specifically to an antigen of interest, e.g. CD38.

The terms "monoclonal antibody" as used herein refers to a preparation of antibody molecules of single molecular composition. A monoclonal antibody composition displays a single binding specificity and affinity for a particular epitope.

"VH" refers to the variable region of an immunoglobulin heavy chain of an antibody, or antibody fragment. "VL" refers to the variable region of the immunoglobulin light chain of an antibody, or antibody fragment.

The term "CD38" refers to the protein known as CD38. Human CD38 has the amino acid sequence of:

```
                                          (SEQ ID NO: 11)
MANCEFSPVSGDKPCCRLSRRAQLCLGVSILVLILVVVLAVVVPRWR

QQWSGPGTTKRFPETVLARCVKYTEIHPEMRHVDCQSVWDAFKGAFI

SKHPCNITEEDYQPLMKLGTQTVPCNKILLWSRIKDLAHQFTQVQRD

MFTLEDTLLGYLADDLTWCGEFNTSKINYQSCPDWRKDCSNNPVSVF

WKTVSRRFAEAACDVVHVMLNGSRSKIFDKNSTFGSVEVHNLQPEKV

QTLEAWVIHGGREDSRDLCQDPTIKELESIISKRNIQFSCKNIYRPD

KFLQCVKNPEDSSCTSEI.
```

"MOR202" an anti-CD38 antibody whose amino acid sequence and DNA sequence is provided in FIG. 4. "MOR202" and "MOR03087" are used as synonyms to describe the antibody shown in FIG. 4. MOR03087 is disclosed in U.S. Pat. No. 8,088,896, which is incorporated by reference in its entirety.

The term "epitope" refers to a region of a molecule which is specifically recognized by an immunoglobulin or T-cell receptor or otherwise interacts with said molecule. Generally epitopes are of chemically active surface groupings of molecules such as amino acids or carbohydrate or sugar side chains and generally may have specific three-dimensional structural characteristics, as well as specific charge characteristics.

The term "cross-competes" refers to an antibody or other binding agent which shares the ability to bind to a specific region of an antigen. In the present disclosure an antibody or other binding agent that is "cross-competitive" has the ability to interfere with the binding of another antibody or other binding agent for CD38 in a standard competitive binding assay. Such an antibody may, according to non-limiting theory, bind to the same or a related or nearby (e.g., a structurally similar or spatially proximal) epitope on the CD38 protein as the antibody with which it competes.

Cross-competition is present if antibody A reduces binding of antibody B at least by 60%, specifically at least by 70% and more specifically at least by 80% and vice versa in comparison to the positive control which lacks one of said antibodies. As the skilled artisan appreciates competition may be assessed in different assay set-ups. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competition uses an ELISA-based approach (e.g. Example 4). Furthermore a high throughput process for "binning" antibodies based upon their cross-competition is described in International Patent Application No. WO2003/48731. Cross-competition is present if the antibody under investigation reduces the binding of MOR202 to CD38 by 60% or more, specifically by 70% or more and more specifically by 80% or more or if MOR202 reduces the binding of said antibody to CD38 by 60% or more, specifically by 70% or more and more specifically by 80% or more. The term "nitrogen mustard" or "nitrogen mustard alkylating agent", as used herein, includes, but is not limited to, cyclophosphamide, ifosfamide, melphalan mechlorethamine, uramustine, chlorambucil or bendamustine. Cyclophosphamide can be administered, e.g., in the form as it is marketed, e.g., under the trademark CYCLOSTIN®; and ifosfamide as HOLOXAN®. Melphalan is currently marketed as Alkeran® for the treatment of multiple myeloma. Melphalan is further known under the synonyms, alanine nitrogen mustard, L-phenylalanine mustard, L-Sarcolysin, L-sarcolysin phenylalanine mustard, L-sarcolysine phenylalanine mustard, phenylalanine nitrogen mustard or the abbreviation L-PAM. Melphalan is a phenylalanine derivative of nitrogen mustard with antineoplastic activity and described to alkylate DNA at the N7 position of guanine and induces DNA inter-strand cross-linkages, resulting in the inhibition of DNA and RNA synthesis and cytotoxicity against both dividing and non-dividing tumor cells. Melphalan belongs to the class of nitrogen mustard alkylating agents.

A "therapeutically effective amount" of a compound or combination refers to an amount sufficient to cure, alleviate or partially arrest the clinical manifestations of a given disease or disorder and its complications. The amount that is effective for a particular therapeutic purpose will depend on the severity of the disease or injury as well as on the weight and general state of the subject. It will be understood that determination of an appropriate dosage may be achieved, using routine experimentation, by constructing a matrix of values and testing different points in the matrix, all of which is within the ordinary skills of a trained physician or clinical scientist.

The present disclosure relates to combinations, pharmaceuticals, and pharmaceutical compositions containing the described combinations.

In an aspect, the combination comprises an antibody specific for CD38 and a nitrogen mustard. In an embodiment the nitrogen mustard is melphalan. In an aspect the combination is synergistic.

In an embodiment the antibody specific for CD38 comprises an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6).

In an embodiment, the antibody comprises a variable heavy chain of the sequence QVQLVESGGGLVQPGGSLRLSCAASGFTFSSYYMNWVRQAPGKGLEWVSGISGDPSN TYYADSVKGRFTISRDNSKNTLYLQMNSLRAEDTAVYYCARDLPLVYTGFAYWGQG TLVTVSS (SEQ ID NO: 7) and a variable light chain of the sequence DIELTQPPSVSVAPGQTARISCSGDNLRHYYVYWYQQKPGQAPVLVIYGDSKRPSGIPE RFSGSNSGNTATLTISGTQAEDEADYYCQTYTGGASLVFGGGTKLTVLGQ (SEQ ID NO: 9).

In an aspect, the combination is useful for the treatment of cancers, e.g. cancers involving tumor cells. In an embodiment, the cancer involving tumor cells comprises multiple myeloma. In a further embodiment, the cancer is selected from chronic lymphocytic leukemia, chronic myelogenous leukemia, acute myelogenous leukemia, and acute lymphocytic leukemia.

In an embodiment, the antibody is a monoclonal antibody. In an embodiment, the antibody is an IgG1.

In an aspect, the combination comprises an antibody fragment specific for CD38. In an embodiment the antibody fragment specific for CD38 comprises an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6).

In an embodiment, the antibody fragment comprises a variable heavy chain of the sequence QVQLVESGGGLVQPGGSLRLSCAASGFTFSSYYMNWVRQAPGKGLEW VSGISGDPSNTYYADSVKGRFTISRDNSKNTLYLQMNSLRAEDTAVYYCARDLPLVYT GFAYWGQGTLVTVSS (SEQ ID NO: 7) and a variable light chain of the sequence DIELTQPPSVSVAPGQTARISCSGDNLRHYYVYWYQQKPGQAPVLVIYGDSKRPSGIPE RFSGSNSGNTATLTISGTQAEDEADYYCQTYTGGASLVFGGGTKLTVLGQ (SEQ ID NO: 9).

In an embodiment, the antibody fragment is selected from an Fv, scFv, dsFv, Fab, Fab' and F(ab')2 fragment.

The two components of the synergistic combination of the present invention, e.g. the antibody specific for CD38 and melphalan, may be administered together, separately, or at the same time or at different times. The combinations are not limited to those which are obtained by physical association of the constituents, but also to those which permit a separate administration, which can be simultaneous or spaced out over a period of time. When administered together, the two components may be formulated together in one pharmaceutical composition, which may include a pharmaceutical acceptable carrier or excipient. Alternatively the two components might also be formulated in different pharmaceutical compositions. In this case the two components can be administered simultaneously or subsequently. In an embodiment, melphalan is administered prior to and/or separately from the administration of the antibody specific for CD38, e.g. MOR202. In a further embodiment, melphalan is administered at least 72 hours prior to administration of the antibody specific for CD38, e.g. MOR202.

In an aspect the pharmaceutical composition is administered intravenously or subcutaneously. In an aspect the pharmaceutical composition is administered in a therapeutically effective amount.

In an aspect the pharmaceutical composition are pharmaceutically acceptable, sterile solutions or suspensions. The sterile aqueous solutions can consist of a solution of the active ingredients in water.

EMBODIMENTS

An aspect of the present disclosure comprises a synergistic combination of an antibody specific for CD38 comprising an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6) and melphalan for the treatment of multiple myeloma.

A further embodiment comprises a synergistic combination of an antibody specific for CD38, wherein the antibody comprises a variable heavy chain of the sequence QVQLVESGGGLVQPGGSLRLSCAASGFTFSSYYMNWVRQAPGKGLEWVSGISGDPSN TYYADSVKGR- FTISRDNSKNTLYLQMNSLRAEDTAVYYCARDL-
PLVYTGFAYWGQG TLVTVSS (SEQ ID NO: 7) and a
variable light chain of the sequence DIELTQPPSVS-
VAPGQTARISCSGDNLRHYYVYWYQQKPGQAPV-
LVIYGDSKRPSGIPE RFSGSNSGNTATLTISGTQAE-
DEADYYCQTYTGGASLVEGGGTKLTVLGQ. (SEQ ID
NO: 9) and melphalan for the treatment of multiple
myeloma.

Another aspect comprises a combination of an antibody specific for CD38 and a nitrogen mustard alkylating agent. In a further embodiment, the combination comprises a nitrogen mustard alkylating agent, which is selected from a group which comprises but is not limited to cyclophosphamide, ifosfamide, melphalan (ALKERAN®), bendamustine (TREAKISYM®, RIBOMUSTIN® and TREANDA®), mechlorethamine, uramustine and chlorambucil. In an embodiment, the nitrogen mustard is melphalan.

Another aspect comprises a combination of an antibody that is specific for CD38 which cross-competes with an antibody comprising an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6) and a nitrogen mustard alkylating agent. In a further embodiment, the combination comprises an nitrogen mustard alkylating agent, which is selected from a group which comprises but is not limited to cyclophosphamide, ifosfamide, melphalan (ALKERAN®), bendamustine (TREAKISYM®, RIBOMUSTIN® and TREANDA®), mechlorethamine, uramustine and chlorambucil. In an embodiment, the nitrogen mustard is melphalan.

Another aspect comprises a combination comprising an antibody specific for CD38 comprising an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6) and melphalan. In an embodiment, melphalan is administered prior to administration of the antibody specific for CD38. In a further embodiment, the melphalan is administered 72 hours prior to administration of the antibody specific for CD38.

In an further embodiment, the combination comprises an antibody specific for CD38 comprising an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6) and an nitrogen mustard alkylating agent. In an embodiment, the nitrogen mustard is melphalan.

Another aspect comprises a method of treating multiple myeloma in an individual in need thereof, which method comprises administration of an antibody specific for CD38 comprising an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6) and a nitrogen mustard alkylating agent to an individual having multiple myeloma. In a further embodiment the nitrogen mustard alkylating agent is selected from a group which comprises but is not limited to cyclophosphamide, ifosfamide, melphalan (Alkeran®), mechlorethamine, bendamustine (TREAKISYM®, RIBOMUSTIN® and TREANDA®), uramustine and chlorambucil. In an embodiment, the nitrogen mustard is melphalan.

Another aspect comprises a method of treating multiple myeloma in an individual in need thereof, which method comprises administration of an antibody specific for CD38 comprising an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6) and melphalan to an individual having multiple myeloma.

Another aspect comprises a method of treating multiple myeloma in an individual in need thereof, which method comprises administration of an antibody that is specific for CD38 which cross-competes with an antibody comprising an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6) and an nitrogen mustard alkylating agent to an individual having multiple myeloma. In a further embodiment the nitrogen mustard alkylating agent is selected from a group which comprises but is not limited to cyclophosphamide, ifosfamide, melphalan (Alkeran®), bendamustine (TREAKISYM®, RIBOMUSTIN® and TREANDA®), mechlorethamine, uramustine and chlorambucil. In an embodiment, the nitrogen mustard is melphalan.

Another aspect comprises a combination of an antibody that is specific for CD38 which cross-competes with an antibody comprising an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6) and an nitrogen mustard alkylating agent for the treatment of multiple myeloma. In a further embodiment the nitrogen mustard alkylating agent is selected from a group which comprises but is not limited to cyclophosphamide, ifosfamide, melphalan (Alkeran®), mechlorethamine, bendamustine (TREAKISYM®, RIBOMUSTIN® and TREANDA®), uramustine and chlorambucil. In a further embodiment the combination is a synergistic combination.

Another aspect comprises a combination of an antibody that is specific for CD38 which cross-competes with an antibody comprising an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6) and melphalan thereof for the treatment of multiple myeloma. In a further embodiment the combination is a synergistic combination.

Another aspect comprises a combination of an antibody that is specific for CD38 which binds to the same epitope as an antibody comprising an HCDR1 of sequence GFTF- SSYYMN (SEQ ID NO: 1), HCDR2 of sequence GIS-GDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6) and melphalan for the treatment of multiple myeloma.

In another aspect, the components of the combination, the antibody specific for CD38 and the nitrogen mustard alkylating agent, are administered separately. In an embodiment, the nitrogen mustard alkylating agent is administered prior to administration of the antibody specific for CD38. In a further embodiment, the nitrogen mustard alkylating agent is administered 72 hours prior to administration of the antibody specific for CD38.

In another aspect, the components of the combination, the antibody specific for CD38 and melphalan, are administered separately. In an embodiment, melphalan is administered prior to administration of the antibody specific for CD38. In a further embodiment, melphalan is administered 72 hours prior to administration of the antibody specific for CD38.

In an embodiment, the combination is used for the treatment of cancer involving tumor cells. In a further embodiment, the cancer is selected from multiple myeloma, chronic lymphocytic leukemia, chronic myelogenous leukemia, acute myelogenous leukemia, and acute lymphocytic leukemia.

EXAMPLES

Example 1

CD38 Expression on the surface of various cell lines. The cell lines of Table 1 were tested for levels of CD38 expression.

TABLE 1

| LP1 | Multiple Myeloma Cell Line, DSMZ #ACC 41 |
| NCI-H929 | Multiple Myeloma Cell Line, DSMZ #ACC 163 |
| RPMI8226 | Multiple Myeloma Cell Line, DSMZ #ACC 402 |

Cells were stained with a directly labelled QuantiBRITE™ CD38-PE antibody (Becton Dickinson GmbH, Clone HB7, CAT #342371), which is specific for CD38. The "Antibodies Bound Per Cell" (ABC's) were determined using the flow cytometry based QuantiBRITE™ system, which measures the geometric mean (GeoMean) per cell. Conversion of measured GeoMean into correlating ABC amount per cell was done with GraphPad PRISM™ software. The ABC values are assumed to correlate with the number of CD38 molecules per cell, since QuantiBRITE™ CD38-PE carries one PE molecule per antibody. The results are shown in Table 2.

TABLE 2

| Experiment | Cell line | ABC |
|---|---|---|
| 4SSR6 | LP1 | 125000 |
| | NCI-H929 | 195000 |
| | RPMI8226 | >677000 |

Example 2

Synergistic Combination of MOR202 and Melphalan in an Orthotopic Osteolysis Model Altogether, 70 female SCID mice were analyzed to determine the Efficacy of Melphalan and MOR03087 alone and in combination against Human Multiple Myeloma NCI-H929 cells.

Solvent Diluent (sodium citrate, propylene glycol, ethanol (96%) and water), provided with Melphalan, was provided to be administered intravenously. Melphalan, supplied as a freeze-dried powder (50 mg per vial) was reconstituted in 5 mL Solvent Diluent and further diluted with Sterile Saline for intravenous administration.

MOR202 in Final Buffer was prepared for intraperitoneal administration.

On day −7, all 70 female SCID mice were inoculated with $2.5 \times 10^6$ NCI-H929 cells (in 5 pl) orthotopically into the right tibia using a 27-gauge half inch needle and a 50 pl Hamilton Syringe.

On Day −4, 3 days post-inoculation, 60 animals were randomised based on body weight into 6 groups of 10 to allow animals to acclimatise to each other. Day −4 was used as a baseline for all body weight assessments over course of study. An additional body weight measurement was taken at Day −2.

Treatments were commenced from Day −1 (6 days post-inoculation) for Melphalan/Vehicle Control treated groups, and on Day 0 for MOR03087 treated groups and were continued for six weeks.

Melphalan, 4 mg/kg or 8 mg/kg was administered 3× weekly for 6 weeks intravenously. MOR202 (3 mg/kg) was administered 3× weekly intraperitoneally for 6 weeks. In the vehicle group Solvent Diluent was administered 2× weekly.

For analysis retro-orbital bleedings were performed on all mice in each group at 2 timepoints, 15-30 min after the 4th and 8th administration of Melphalan and 25 hr after the 5th and 11th administration of MOR03087 for the preparation of serum. Samples were aliquoted into 3 vials (25 uL+25 uL+rest) and stored at −80° C.

Body weight measurements were taken 3 times per week +/−1 hr from initial time point. Treatment period is 6 weeks, after which study will be terminated.

Figure 1:
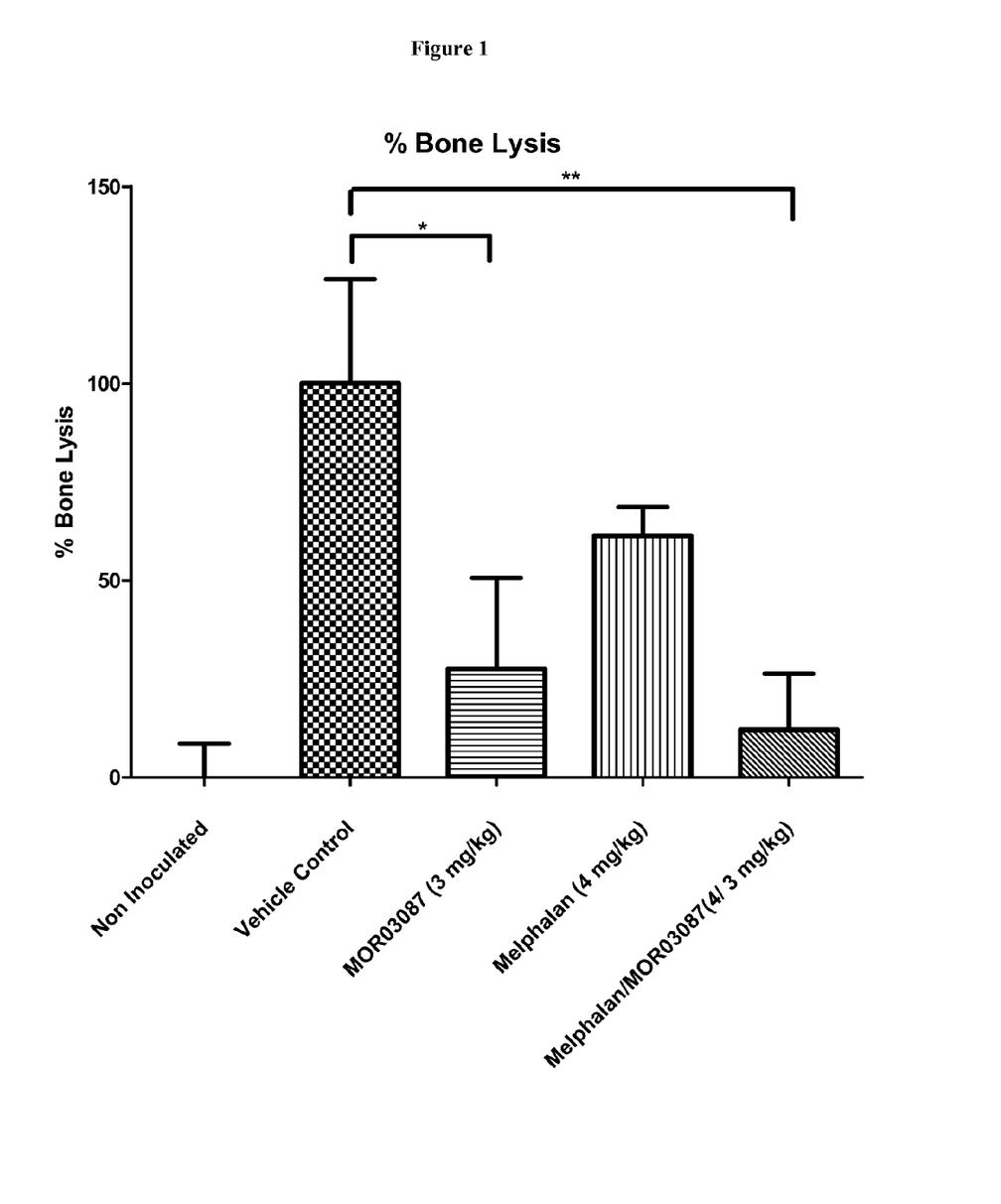
FIG. 1 shows the MicroCT Scan mean total bone volume of each of the study groups described in Example 3. In every group 3.0 mg/kg of MOR03087 and 4.0 mg/kg of melphalan were used.
Figure 2:
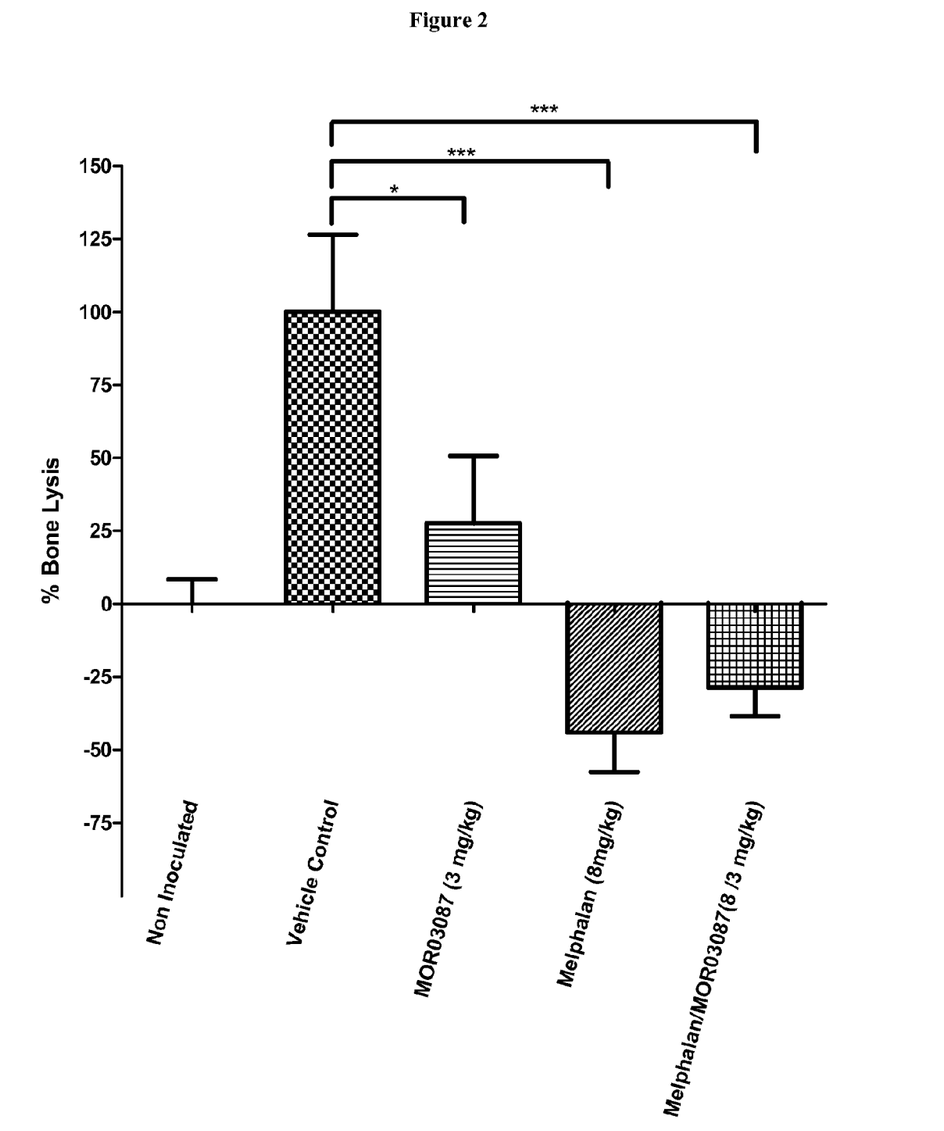
FIG. 2 shows the MicroCT Scan mean total bone volume of each of the study groups described in Example 3. In every group 3.0 mg/kg of MOR03087 and 8.0 mg/kg of melphalan were used.

Upon termination of the study (day 42), cardiac end-bleeds were performed from all animals for the preparation of serum. Furthermore, the left and the right tibia were excised from all animals and fixed in 10% Neutral Buffered Formalin for microCT analysis. Respective results of microCT analysis are shown in FIG. 1 (4 mg/kg Melphalan) and FIG. 2 (8 mg/kg Melphalan). In both experimental set ups a superior effect based on synergism was observed if Melphalan and MOR202 were subjected in combination. The statistical calculation to prove a synergistic effect of the combinatorial therapy using MOR202 and Melphalan was performed using the Clarke Theorem and is summarized in Table 3. For the experimental set up using 8 mg/kg the analysis of a synergistic effect calculation was obsolete since Melphalan alone already reduced bone lysis completely (FIG. 2).

Clarke et al. Synergism

Synergism was determined using the methods described in Clarke et al., issues in experimental design and endpoint analysis in the study of experimental cytotoxic agents in vivo in breast cancer and other models, Breast Cancer Research and Treatment 46:255-278 (1997), which is incorporated by reference in its entirety.

The data is analysed in the following way:

Antagonistic=$(AB)/C \geq (A/C) \times (B/C)$

Additive $(AB)/C=(A/C) \times (B/C)$

Synergistic=$(AB)/C \leq (A/C) \times (B/C)$

Where A is response to treatment 1; B is response to treatment 2; C is response to no treatment vehicle; AB is combination of treatments A and B.

TABLE 3

Calculation of synergism using the Clarke Theorem based on the data in FIG. 1

|  | Total Bone Lysis [%] |
|---|---|
| A: Melphalan alone [4 mg/kg] | 61.3 |
| B: MOR03087 alone [3 mg/kg] | 27.6 |
| C: Vehicle Control | 100.0 |
| AB: Combination | 12.1 |
| (AB)/C [%] = observed combinatorial effect | 12.1 |
| (A/C) × (B/C) [%] = theoretical additive effect | 16.9 |
| Conclusion | Synergy |

CONCLUSION

Since 16.9 ((A/C) is bigger than 12.1 ((A/B)/C), according to Clarke et al., a synergistic effect is of MOR03087 and Melphalan is demonstrated.

Example 3

Figure 3:
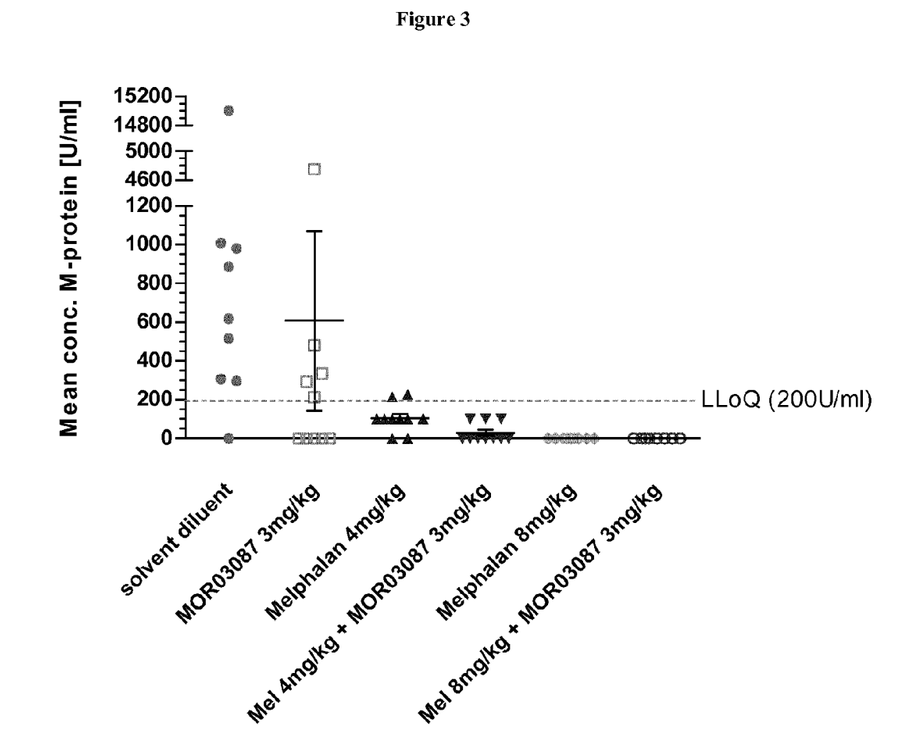
FIG. 3 shows the mean Protein M concentration in sera isolated from mice from an orthotopic osteolysis model using a CD38 antibody (MOR03087) and melphalan and a combination thereof.

Detection of M-Protein Concentration in Sera Isolated from Mice on Day 42 of the Orthotopic Osteolysis Model Additionally, sera isolated upon termination of the study were analyzed for Protein M content via ELISA. In contrast to the sera isolated from mice that received solvent diluent only, the Protein M concentration was significantly reduced in sera isolated from mice treated with Melphalan, MOR202 or a combination thereof. Results are summarized in FIG. 3.

Example 4

ELISA-Based Cross-Competition Assay

Cross-competition of an anti-CD38 antibody or another CD38 binding agent may be detected by using an ELISA assay according to the following standard procedure.

The general principle of the ELISA-assay involves coating an anti-CD38 antibody onto the wells of an ELISA plate. An excess amount of a second, potentially cross-competitive, anti-CD38 antibody is then added in solution (i.e. not bound to the ELISA plate). Subsequently a limited amount of CD38-Fc is then added to the wells.

The antibody which is coated onto the wells and the antibody in solution will compete for binding of the limited number of CD38 molecules. The plate is then washed to remove CD38 molecules that has not bound to the coated antibody and to also remove the second, solution phase, antibody as well as any complexes formed between the second, solution phase antibody and CD38. The amount of bound CD38 is then measured using an appropriate CD38 detection reagent. Therefore CD38 may be fused with a tag, like e.g. Fc, Flag, etc. which can be detected via an appropriate tag-specific antibody.

An antibody in solution that is cross-competitive to the coated antibody will be able to cause a decrease in the number of CD38 molecules that the coated antibody can bind relative to the number of Cd38 molecules that the coated antibody can bind in the absence of the second, solution phase antibody.

This assay is described in more detail further below for two antibodies termed Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y CD38 binding sites per well are at least 10 fold higher than the moles of Ab-X CD38 binding sites that are used, per well, during the coating of the ELISA plate. CD38 is then added such that the moles of CD38 added per well were at least 25-fold lower than the moles of Ab-X CD38 binding sites that are used for coating each well. Following a suitable incubation period, the ELISA plate is washed and a CD38 detection reagent is added to measure the amount of CD38 molecules specifically bound by the coated anti-CD38 antibody (in this case Ab-X). The background signal for the assay is defined as the signal obtained in wells with the coated antibody (in this case Ab-X), second solution phase antibody (in this case Ab-Y), buffer only (i.e. no CD38) and CD38 detection reagents. The positive control signal for the assay is defined as the signal obtained in wells with the coated antibody (in this case Ab-X), second solution phase antibody buffer only (i.e. no second solution phase antibody), CD38 and CD38 detection reagents. The ELISA assay needs to be run in such a manner so as to have the positive control signal be at least 6 times the background signal.

To avoid any artifacts (e.g. significantly different affinities between Ab-X and Ab-Y for CD38) resulting from the choice of which antibody to use as the coating antibody and which to use as the second (competitor) antibody, the cross-blocking assay needs to be run in two formats: 1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

We claim:

1. A pharmaceutical composition comprising a combination of (i) an antibody specific for CD38 comprising an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6) and (ii) melphalan for the treatment of multiple myeloma.

2. A pharmaceutical composition according to claim 1, wherein the antibody comprises a variable heavy chain of the sequence:

(SEQ ID NO: 7)
QVQLVESGGGLVQPGGSLRLSCAASGFTFSSYYMNWVRQAPGKGLEW

VSGISGDPSNTYYADSVKGRFTISRDNSKNTLYLQMNSLRAEDTAVY

YCARDLPLVYTGFAYWGQGTLVTVSS;

and a variable light chain of the sequence:

(SEQ ID NO: 9)
DIELTQPPSVSVAPGQTARISCSGDNLRHYYVYWYQQKPGQAPVLVI

YGDSKRPSGIPERFSGSNSGNTATLTISGTQAEDEADYYCQTYTGGA

SLVFGGGTKLTVLGQ.

3. A pharmaceutical composition according to claim 1, wherein the antibody specific for CD38 and melphalan are administered separately.

4. A pharmaceutical composition according to claim 3, wherein melphalan is administered prior to administration of the antibody specific for CD38.

5. A pharmaceutical composition according to claim 4, wherein melphalan is administered 72 hours prior to administration of the antibody specific for CD38.

6. A method of treating multiple myeloma in an individual in need thereof, which comprises administration of (i) an antibody specific for CD38 comprising an HCDR1 of sequence GFTFSSYYMN (SEQ ID NO: 1), HCDR2 of sequence GISGDPSNTYYADSVKG (SEQ ID NO: 2), HCDR3 of sequence DLPLVYTGFAY (SEQ ID NO: 3), LCDR1 of sequence SGDNLRHYYVY (SEQ ID NO: 4), LCDR2 of sequence GDSKRPS (SEQ ID NO: 5), and LCDR3 of sequence QTYTGGASL (SEQ ID NO: 6) and (ii) melphalan to an individual having multiple myeloma.

7. A method of treatment according to claim 6, wherein the antibody specific for CD38 and melphalan are administered separately.

8. A method of treatment according to claim 7, wherein melphalan is administered prior to administration of the antibody specific for CD38.

9. A method of treatment according to claim 8, wherein melphalan is administered 72 hours prior to administration of the antibody specific for CD38.

10. A pharmaceutical composition according to claim 2, wherein the antibody specific for CD38 and melphalan are administered separately.

11. A pharmaceutical composition according to claim 10, wherein melphalan is administered prior to administration of the antibody specific for CD38.

12. A pharmaceutical composition according to claim 11, wherein melphalan is administered 72 hours prior to administration of the antibody specific for CD38.

13. A method of treatment according to claim 6, wherein the antibody comprises a variable heavy chain of the sequence:
QVQLVESGGGLVQPGGSL RLSCAASGFTFSSYYM-NWVRQAPGKGLEW VSGISGDPSNTYYADSVKG RFTISRDNSKNTLYLQMNSLRAEDTAVY YCARDLPLVYTGFAYWGQG TLVTVSS (SEQ ID NO: 7);
and a variable light chain of the sequence:
DIELTQPPSVSVAPGQTARISCSGDNLRHYYVYWY-QQKPGQAPVLVI YGDSKRPSGIPERFSGSNSGN-TATLTISGTQAEDEADYYCQTYTGGA SLVF-GGGTKLTVLGQ (SEQ ID NO: 9).

14. A method of treatment according to claim 13, wherein the antibody specific for CD38 and melphalan are administered separately.

15. A method of treatment according to claim 14, wherein melphalan is administered prior to administration of the antibody specific for CD38.

16. A method of treatment according to claim 15, wherein melphalan is administered 72 hours prior to administration of the antibody specific for CD38.

* * * * *

SEQUENCE LISTING

```
<160> NUMBER OF SEQ ID NOS: 11

<210> SEQ ID NO 1
<211> LENGTH: 10
<212> TYPE: PRT
<213> ORGANISM: Homo sapiens
<220> FEATURE:
```

-continued

<223> OTHER INFORMATION: HCDR1 of anti-CD38 antibody

<400> SEQUENCE: 1

Gly Phe Thr Phe Ser Ser Tyr Tyr Met Asn
1               5                   10

<210> SEQ ID NO 2
<211> LENGTH: 17
<212> TYPE: PRT
<213> ORGANISM: Homo sapiens
<220> FEATURE:
<223> OTHER INFORMATION: HCDR2 of anti-CD38 antibody

<400> SEQUENCE: 2

Gly Ile Ser Gly Asp Pro Ser Asn Thr Tyr Tyr Ala Asp Ser Val Lys
1               5                   10                  15

Gly

<210> SEQ ID NO 3
<211> LENGTH: 11
<212> TYPE: PRT
<213> ORGANISM: Homo sapiens
<220> FEATURE:
<223> OTHER INFORMATION: HCDR3 of anti-CD38 antibody

<400> SEQUENCE: 3

Asp Leu Pro Leu Val Tyr Thr Gly Phe Ala Tyr
1               5                   10

<210> SEQ ID NO 4
<211> LENGTH: 11
<212> TYPE: PRT
<213> ORGANISM: Homo sapiens
<220> FEATURE:
<223> OTHER INFORMATION: LCDR1 of anti-CD38 antibody

<400> SEQUENCE: 4

Ser Gly Asp Asn Leu Arg His Tyr Tyr Val Tyr
1               5                   10

<210> SEQ ID NO 5
<211> LENGTH: 7
<212> TYPE: PRT
<213> ORGANISM: Homo sapiens
<220> FEATURE:
<223> OTHER INFORMATION: LCDR2 of anti-CD38 antibody

<400> SEQUENCE: 5

Gly Asp Ser Lys Arg Pro Ser
1               5

<210> SEQ ID NO 6
<211> LENGTH: 8
<212> TYPE: PRT
<213> ORGANISM: Homo sapiens
<220> FEATURE:
<223> OTHER INFORMATION: LCDR3 of anti-CD38 antibody

<400> SEQUENCE: 6

Gln Thr Tyr Thr Gly Gly Ala Ser
1               5

<210> SEQ ID NO 7
<211> LENGTH: 120
<212> TYPE: PRT
<213> ORGANISM: Homo sapiens
<220> FEATURE:
<223> OTHER INFORMATION: MOR202 Variable Heavy Domain

<400> SEQUENCE: 7

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Tyr Met Asn Trp Val Arg Gln Ala Pro Gly Lys Gly Leu Glu Trp Val
         35                  40                  45

Ser Gly Ile Ser Gly Asp Pro Ser Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
        115                 120
```

<210> SEQ ID NO 8
<211> LENGTH: 360
<212> TYPE: DNA
<213> ORGANISM: Homo sapiens
<220> FEATURE:
<223> OTHER INFORMATION: MOR202 Variable Heavy Domain

<400> SEQUENCE: 8

```
caggtgcaat tggtggaaag cggcggcggc ctggtgcaac cgggcggcag cctgcgtctg     60
agctgcgcgg cctccggatt tacctttttct tcttattata tgaattgggt gcgccaagcc   120
cctgggaagg gtctcgagtg ggtgagcggt atctctggtg atcctagcaa taccttattat   180
gcggatagcg tgaaaggccg ttttaccatt tcacgtgata attcgaaaaa caccctgtat   240
ctgcaaatga acagcctgcg tgcggaagat acggccgtgt attattgcgc gcgtgatctt   300
cctcttgttt atactggttt tgcttattgg ggccaaggca ccctggtgac ggttagctca   360
```

<210> SEQ ID NO 9
<211> LENGTH: 109
<212> TYPE: PRT
<213> ORGANISM: Homo sapiens
<220> FEATURE:
<223> OTHER INFORMATION: MOR202 Variable Light Domain

<400> SEQUENCE: 9

```
Asp Ile Glu Leu Thr Gln Pro Pro Ser Val Ser Val Ala Pro Gly Gln
  1               5                  10                  15

Thr Ala Arg Ile Ser Cys Ser Gly Asp Asn Leu Arg His Tyr Tyr Val
             20                  25                  30

Tyr Trp Tyr Gln Gln Lys Pro Gly Gln Ala Pro Val Leu Val Ile Tyr
         35                  40                  45

Gly Asp Ser Lys Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Thr Tyr Thr Gly Gly Ala Ser Leu
                 85                  90                  95
```

Val Phe Gly Gly Gly Thr Lys Leu Thr Val Leu Gly Gln
            100                 105

<210> SEQ ID NO 10
<211> LENGTH: 327
<212> TYPE: DNA
<213> ORGANISM: Homo sapiens
<220> FEATURE:
<223> OTHER INFORMATION: MOR202 Variable Light Domain

<400> SEQUENCE: 10

```
gatatcgaac tgacccagcc gccttcagtg agcgttgcac caggtcagac cgcgcgtatc      60
tcgtgtagcg gcgataatct tcgtcattat tatgttattg gtaccagca gaaacccggg      120 caggcgccag ttcttgtgat ttatggtgat tctaagcgtc cctcaggcat cccggaacgc     180
tttagcggat ccaacagcgg caacaccgcg accctgacca ttagcggcac tcaggcggaa     240
gacgaagcgg attattattg ccagacttat actggtggtg cttctcttgt gtttggcggc     300
ggcacgaagt taaccgttct tggccag                                          327
```

<210> SEQ ID NO 11
<211> LENGTH: 300
<212> TYPE: PRT
<213> ORGANISM: Homo sapiens
<220> FEATURE:
<223> OTHER INFORMATION: Human CD38 amino acid sequence

<400> SEQUENCE: 11

Met Ala Asn Cys Glu Phe Ser Pro Val Ser Gly Asp Lys Pro Cys Cys
 1               5                  10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
            100                 105                 110

Gly Thr Gln Thr Val Pro Cys Asn Lys Ile Leu Leu Trp Ser Arg Ile
        115                 120                 125

Lys Asp Leu Ala His Gln Phe Thr Gln Val Gln Arg Asp Met Phe Thr
130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
        195                 200                 205

Asn Gly Ser Arg Ser Lys Ile Phe Asp Lys Asn Ser Thr Phe Gly Ser
    210                 215                 220

Val Glu Val His Asn Leu Gln Pro Glu Lys Val Gln Thr Leu Glu Ala
225                 230                 235                 240

-continued

```
Trp Val Ile His Gly Gly Arg Glu Asp Ser Arg Asp Leu Cys Gln Asp
            245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
    290                 295                 300
```